(12) United States Patent
Gridelet et al.

(10) Patent No.: US 8,821,794 B2
(45) Date of Patent: Sep. 2, 2014

(54) SENSOR CHIP AND METHOD OF MANUFACTURING THE SAME

(75) Inventors: Evelyne Gridelet, Omal (BE); Franciscus Widdershoven, Eindhoven (NL); Pablo Garcia Tello, Leuven (BE); Magali Lambert, Versailles (FR)

(73) Assignee: NXP, B.V., Eindhoven (NL)

( * ) Notice: Subject to any disclaimer, the term of this patent is extended or adjusted under 35 U.S.C. 154(b) by 84 days.

(21) Appl. No.: 12/934,827

(22) PCT Filed: Mar. 19, 2009

(86) PCT No.: PCT/IB2009/051156
§ 371 (c)(1),
(2), (4) Date: Sep. 27, 2010

(87) PCT Pub. No.: WO2009/122314
PCT Pub. Date: Oct. 8, 2009

(65) Prior Publication Data
US 2011/0027128 A1 Feb. 3, 2011

(30) Foreign Application Priority Data
Mar. 31, 2008 (EP) .................... 08103203

(51) Int. Cl.
*G01N 27/00* (2006.01)
*G01N 33/543* (2006.01)
*G01N 27/22* (2006.01)

(52) U.S. Cl.
CPC .......... *G01N 33/5438* (2013.01); *G01N 27/226* (2013.01)
USPC .................. 422/82.01; 422/82.02; 435/287.1; 435/287.2

(58) Field of Classification Search
USPC ........... 435/285.2, 287.1–287.2; 257/84, 414; 422/82.01, 68.1, 82.05, 82.02–82.04
See application file for complete search history.

(56) References Cited

U.S. PATENT DOCUMENTS

| | | | |
|---|---|---|---|
| 5,891,756 A * | 4/1999 | Erickson | 438/108 |
| 6,001,673 A | 12/1999 | Marcinkiewicz | |
| 6,395,454 B1 | 5/2002 | Piscevic | |
| 6,969,449 B2 * | 11/2005 | Maher et al. | 204/403.01 |
| 6,995,475 B2 * | 2/2006 | Biggs et al. | 257/784 |
| 7,015,011 B2 * | 3/2006 | Hibbs | 435/29 |
| 7,084,499 B2 * | 8/2006 | Shen | 257/737 |

(Continued)

FOREIGN PATENT DOCUMENTS

| WO | 03074683 A1 | 9/2003 |
|---|---|---|
| WO | 2008/132656 A2 | 11/2008 |

OTHER PUBLICATIONS

Eversmann et al. (IEEE Journal of Solid-State circuits, IEEE Service Centervol. 38, No. 12 Dec. 1, 2003 pp. 2306-2317).*

(Continued)

*Primary Examiner* — Jan Ludlow

(57) ABSTRACT

A sensor chip (100) for detecting particles, the sensor chip (100) comprising a substrate (102), an electric connection structure (104) arranged in a surface portion of the substrate (102) and adapted for an electric connection to an electric connection element (106), a sensor active region (108) arranged in another surface portion of the substrate (102) and being sensitive to the presence of the particles to be detected, and a continuous dielectric layer (110) covering the substrate (102) including covering the electric connection structure (104) and the sensor active region (108).

21 Claims, 2 Drawing Sheets

(56) References Cited

U.S. PATENT DOCUMENTS

| | | | |
|---|---|---|---|
| 7,317,216 B2* | 1/2008 | Holm-Kennedy | 257/253 |
| 7,425,749 B2* | 9/2008 | Hartzell et al. | 257/414 |
| 7,521,812 B2* | 4/2009 | Lee et al. | 257/784 |
| 2006/0261446 A1* | 11/2006 | Wood et al. | 257/621 |

OTHER PUBLICATIONS http://homepages.rpi.edu/~schubert/Educational-resources/Materials-Hardness.pdf (Oct. 1, 2013).* http://en.wikipedia.org/wiki/Copper (Oct. 1, 2013).* http://en.wikipedia.org/wiki/Silicon_nitride (Oct. 1, 2013).*

Eversmann, Bjoern, et al; "CMOS Sensor Array for Electrical Imaging of Neuronal Activity"; IEEE Intl Symposium on Circuits and Systems, vol. 4; p. 3479-3482 (May 23-26, 2005).

Interntional Search Report and Written Opinion for Application PCT/IB2009/051156 (Mar. 19, 2009).

Hofmann, Franz, et al; "Technology Aspects of a CMOS Neuro-Sensor: Back End Process and Packaging"; European Solid-State Device Research, IEEE, Piscataway, NJ, US; pp. 167-170; (Sep. 16, 2003).

Brederlow, Ralf, et al; "A 128 x 128 CMOS Biosensor Array for Extra Cellular Recording of Neural Activity"; IEEE Journal of Solid-State Circuits, IEEE Service Center, Piscataway, NJ, US; vol. 38, No. 12; pp. 2306-2317; (Dec. 1, 2003).

Aoh, Jong-Ning; Thermosonic Bonding of Gold Wire Onto a Copper Pad With Titanium Thin-Film Deposition; Minerals, Metals & Materials Society; 7 Pages (Apr. 2004).

Besel, Brigitte, et al; "Transistor Array With an Organotypic Brain Slice, Field Potential Records and Synaptic Currents"; European Journal of Neuroscience Societies, vol. 15, No. 6; pp. 999-1005 (Mar. 2003).

* cited by examiner

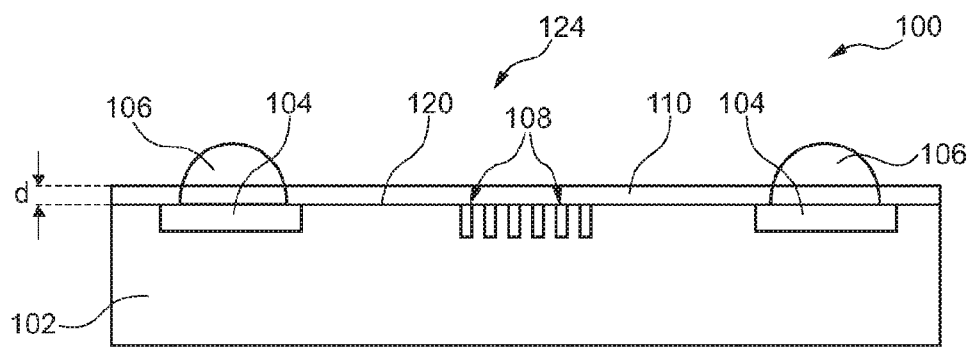
Fig. 1
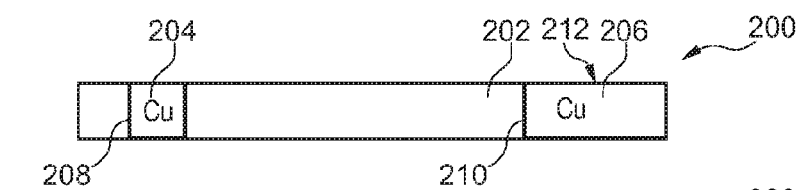
Fig. 2
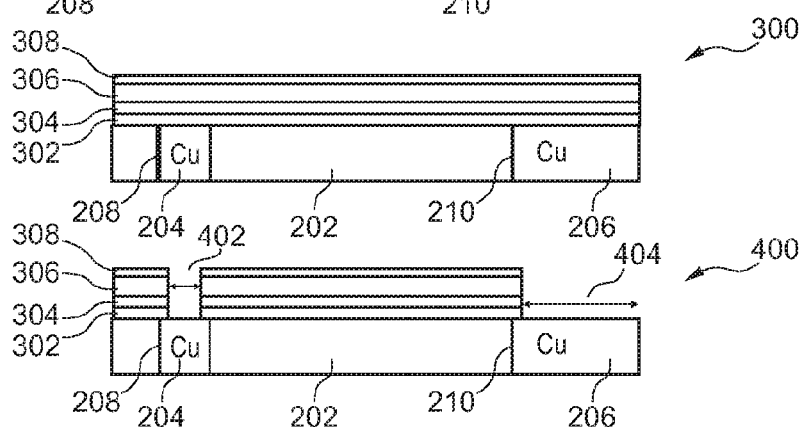
Fig. 3
Fig. 4
Fig. 5
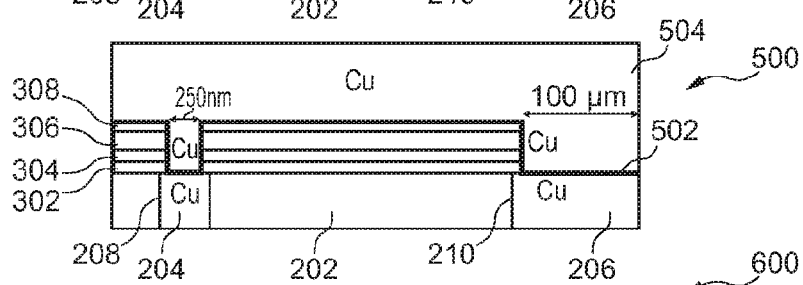
Fig. 6
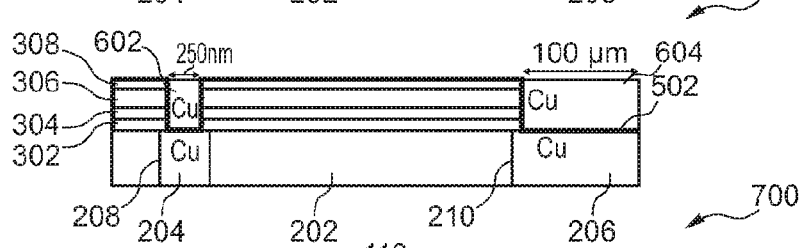
Fig. 7
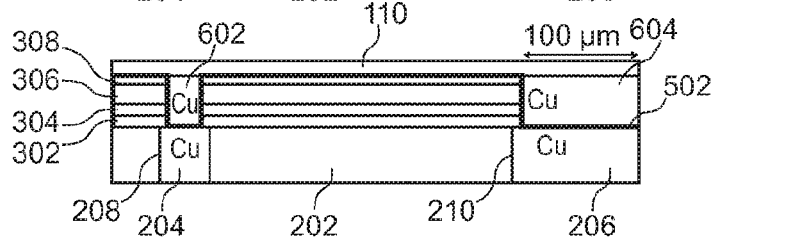

SENSOR CHIP AND METHOD OF MANUFACTURING THE SAME

FIELD OF THE INVENTION

The invention relates to a sensor chip.

Moreover, the invention relates to a method of manufacturing a sensor chip.

BACKGROUND OF THE INVENTION

A sensor chip for detecting particles may be a biosensor, which may be used for detecting an analyte and may combine a biological component with a physicochemical or physical detector component.

For instance, a biosensor may be based on the phenomenon that capture particles immobilized on a surface of a biosensor, may selectively attach with target particles in a fluidic sample, for instance when an antibody-binding fragment of an antibody or the sequence of a DNA single strand as a capture particle fits to a corresponding sequence or structure of a target particle. When such attachment or sensor events occur at the sensor surface, this may change the electrical properties of the surface which can be detected as the sensor event.

WO 2003/074683 discloses a biochip for capacitive stimulation and/or detection of biological tissue, having a carrier structure, at least one stimulation and/or sensor device that is arranged in or on the carrier structure, at least one dielectric layer, one of the surfaces of said layer being arranged in the stimulation and/or sensor device while the opposite surface of said layer forms a stimulation and/or sensor surface for capacitive stimulation and/or detection of biological tissue, wherein the continuous dielectric layer contains $TiO_2$.

Conventional biosensor chips usually have a sensing surface on top of a processed semiconductor structure. This may also involve the exposure of various metal layers on a surface of such a biosensor chip such as detection electrodes, bonding pads, etc.

OBJECT AND SUMMARY OF THE INVENTION

It is an object of the invention to provide a robust sensor.

In order to achieve the object defined above, a sensor chip and a method of manufacturing a sensor chip according to the independent claims are provided.

According to an exemplary embodiment of the invention, a sensor chip (for instance a monolithically integrated sensor chip) for detecting particles (for instance biological molecules) is provided, the sensor chip comprising a substrate, an electric connection structure (for instance for supplying electric signals and/or power from a periphery device to the sensor chip and/or for supplying electric signals from the sensor chip, particularly an electric sensor signal indicative of a sensor event, to a periphery device) arranged in a surface portion of the substrate and adapted for an electric connection to an electric connection element (for instance to be electrically coupled to a periphery device external of the chip), a sensor active region (such as a sensor electrode being influencable regarding properties such as capacity or effect of charge by the presence or absence of particles to be sensed) arranged in another surface portion of the substrate and being sensitive to the presence of the particles to be detected, and a continuous (for instance single-material) dielectric layer (particularly electrically insulating) covering (for instance an entire upper surface of) the substrate including covering the electric connection structure and the sensor active region.

According to another exemplary embodiment of the invention, a method of manufacturing a sensor chip is provided, the method comprising providing a substrate, arranging an electric connection structure in a surface portion of the substrate and adapting the electric connection structure for an electric connection to an electric connection element, arranging a sensor active region in another surface portion of the substrate to be sensitive to the presence of the particles to be detected, and forming a continuous dielectric layer covering the substrate including covering the electric connection structure and the sensor active region.

The term "sensor" may particularly denote any device, which may be used for the detection of an analyte. Examples for sensors, which may be realized according to exemplary embodiments, are gas sensors, smoke sensors, biosensors, pH sensors, humidity sensors, etc.

The term "biosensor" may particularly denote any device, which may be used for the detection of a component of an analyte comprising biological particles such as DNA, RNA, proteins, enzymes, cells, bacteria, virus, etc. A biosensor may combine a biological component (for instance capture particles at a sensor active surface capable of detecting particles) with a physicochemical or physical detector component (for instance a capacitor having an electric characteristic which is modifiable by a sensor event).

The term "sensor chip" may particularly denote that a sensor built with the help of micro- or nano-technologies like lithography, etch or deposition techniques. It may particularly denote an integrated circuit, that is to say an electronic chip, particularly in semiconductor technology, more particularly in silicon semiconductor technology, still more particularly in CMOS technology. A monolithically integrated sensor chip has the property of very small dimensions due to the use of micro- or nano-processing technology, and may therefore have a large spatial resolution and a high signal-to-noise ratio particularly when the dimensions of the sensor chip or more precisely of components thereof approach or reach the order of magnitude of micrometers or less, for instance in case of a biosensor reaching the dimensions of biological particles.

The term "sensor active region" may particularly denote a region of a sensor, which may be functionally coupled with a fluidic sample so that a detection event may occur in vicinity of the sensor active region. In other words, the sensor active region may be influenced by processes, which take place in case of a sensing event. A corresponding sensing principle may be an indirect electrical sensing principle (that is a change of the electric properties of the sensor active region).

The term "substrate" may denote any suitable material, such as a semiconductor, glass, plastic, etc. According to an exemplary embodiment, the term "substrate" may be used to define generally the elements for layers that underlie and/or overlie a layer or portions of interest. Also, the substrate may be any other base on which a layer is formed.

The term "fluidic sample" may particularly denote any subset of the phases of matter. Such fluids may include liquids, gases, plasmas and, to some extent, solids, as well as mixtures thereof. Examples for fluidic samples are DNA containing fluids, cells containing fluids, blood, interstitial fluid in subcutaneous tissue, muscle or brain tissue, urine or other body fluids. For instance, the fluidic sample may be a biological substance. Such a substance may comprise proteins, polypeptides, nucleic acids, DNA strands, etc.

The term "particle" may particularly denote a molecule, an organic molecule, a biological particle, DNA, RNA, a protein, an amino acid, a bead, a nano-bead, a nano-tube, etc.

The term "biological particles" may particularly denote any particles which play a significant role in biology or in biological or biochemical procedures, such as genes, DNA, RNA, proteins, enzymes, cells, bacteria, virus, etc.

The term "Back End of the Line" (BEOL) may particularly denote a portion of an integrated circuit fabrication where active components (such as transistors) are interconnected with wiring on the wafer. BEOL generally begins when a first layer of metal is deposited on the processed wafer. It includes contacts, insulator, metal levels, and bonding sites for chip-to-package connections. In contrast to this, the term "Front End of the Line" (FEOL) may particularly denote a first portion of an integrated circuit fabrication where the individual devices (such as transistors) are built. FEOL generally covers everything up to (but not including) the deposition of metal layers. The Back End of the Line portion may be located directly on top of the Front End of the Line portion (in a spatial direction which corresponds to the manufacturing procedure).

The term "bonding" may particularly denote wire bonding, ball bonding, wedge bonding, stud bumping and/or other chip assembly and packaging technologies.

According to an exemplary embodiment of the invention, a monolithically integrated sensor is provided having a top surface which may be covered for instance entirely with an uninterrupted conformally deposited single material electrical insulating layer formed to passivate the sensor surface. Such a dielectric layer may particularly cover an electric connection structure such as contact pads for connecting a bonding connection or the like. The dielectric layer may be formed sufficiently thin to allow bonding through the continuous dielectric layer. Moreover, such a continuous dielectric layer may cover also a sensor active region such as a sensor electrode of a capacitive sensor, so that the sufficiently thin dielectric layer does not significantly disturb interaction between particles above the dielectric layer and the electrode structures below it. By taking this measure, a corrosion protection for the metal structures may be combined with maintenance of a proper sensor performance, whereas a smooth surface may be provided which may also equilibrate surface roughness.

According to an exemplary embodiment of the invention, the same dielectric layer may be used on the bonding region and the sensing region. A continuous dielectric layer may be arranged on top of a sensor, which may be made of CMOS technology. Thus, a sensor may be provided comprising a region for sensing molecules, bond pads and a dielectric layer covering both the sensing region and the bond pads.

According to an exemplary embodiment of the invention, a sensing device may be provided comprising a sensing region adapted for sensing biological material; and a bonding region adapted to place a (bond) connection thereon, wherein both regions are covered with a (continuous) dielectric layer material. In an embodiment, the dielectric layer material may be constituted such as to reduce or minimize its influence on the detection at the sensing region, enable the bonding/bumping through it at the bonding region, and/or be a high-k material in case of a capacitive sensor to reduce or minimize its influence on the electrode capacitance.

Taking the above and other measures may result in the advantages that a protective layer for metallic electrodes and bond pads may be provided, only one material has to brought in contact with the external world, no leakage of liquid into the chip may occur (even when the chip contains porous materials), a smooth and well-controlled electrode surface may be obtained, and deposition may be doable with low-cost deposition tools (that is to say does not have to be fabcompatible).

Next, further exemplary embodiments of the sensor chip will be explained. However, these embodiments also apply to the method of manufacturing a sensor chip.

Exemplary embodiments of the sensor chip may be combined advantageously with the embodiments of unpublished EP 07107118.7, filed Apr. 27, 2007.

The sensor chip may comprise the electric connection element being electrically connected to the electric connection structure through the non-patterned continuous dielectric layer. Such an electric connection element may be a bumping structure or a bonding structure, for example a bonding wire. The electric connection structure embedded close to the surface of the sensor chip below the continuous dielectric layer may be a bond pad. Packaging and interconnect bonding of the chip will not be negatively influenced by the continuous dielectric layer, particularly when the latter is sufficiently thin, for instance less than 4 nm thick.

The continuous dielectric layer may comprise a high-k material. The term high-k dielectric may refer to a material with a sufficiently high dielectric constant (as compared to, for instance silicon dioxide) used in semiconductor manufacturing processes. However, according to an exemplary embodiment, the continuous dielectric layer may also be formed from silicon dioxide. The implementation of high-k material may allow increasing only slightly the sensing electrode capacitance without leakage effects, which may be particularly advantageous for capacitive sensors. Examples for usable high-k materials are tantalum oxide, aluminium oxide, or silicon carbide.

The continuous dielectric layer may have a thickness in a range between basically 1 nm and basically 50 nm, particularly may have a thickness in a range between basically 2 nm and basically 10 nm. The thickness may be less than 5 nm. A small thickness has the advantage of a still proper electric coupling between the embedded metal structures and structures above the dielectric and/or a fluidic sample above the dielectric.

The continuous dielectric layer may be a stack of several materials.

The continuous dielectric layer may be made of a suitable material for sensing.

The sensor active region may comprise one or more sensor electrodes. Such a sensor electrode may form part of a capacitive sensor, for instance may serve as one capacitor plate of the capacitive sensor.

The electric connection structure and/or the sensor active region may comprise a metal such as aluminium. However, it may be preferred to use copper as a material for the electric connection structure and/or the sensor active region since copper is compatible with the small features of the manufacturing procedure of the sensor chip, and may be protected by the dielectric cover structure against corrosion by the fluidic sample above.

The continuous dielectric layer may comprise a biocompatible material. This may denote a material property of the continuous dielectric layer being formed of a material, which is compatible to perform with a host response that is suitable in a specific application. Biocompatibility may also denote the quality of not having toxic or injurious effects on biological systems.

The continuous dielectric layer may comprise an impermeable material. Such a material may be essentially free of pores and may prevent a fluidic, for instance liquid, sample above the layer to penetrate in or through the layer. It may prevent materials from the sensor to penetrate into the fluidic sample and to contaminate the fluidic sample. This may be important for sensors in contact with living elements like cells or for implantable sensors.

The sensor chip may be adapted as a biosensor chip. Particularly, capture molecules and/or a self-assembled monolayer and/or functionalization layer may be arranged on a portion of the dielectric layer above a surface of the sensor active region. The capture particles may be adapted for attachment with the particles to be detected. For example, single stranded DNA may be immobilized over the sensor active region, for instance on the dielectric layer. In the presence of complementary DNA particles as the particles in a sample, an attachment (for instance a hybridization) event may occur so that double stranded DNA is formed over the sensor active region.

The sensor active region may be arranged at an upper surface of a Back End of the Line of the sensor chip. The term "upper" may refer to the order according to which the sensor device is manufactured (so that the FEOL forms a lower portion and the BEOL forms an upper portion of the sensor device). Therefore, the sensor active region may be close to a surface of the sensor chip, which may be brought in an interaction with a fluidic sample to be analyzed. Particularly, a stack of a plurality of layers, involving a plurality of electrically conductive connection elements (such as vias and/or metallization structures) may be provided to separate the sensor active region from a readout member (such as a field effect transistor in the FEOL) spatially, but to couple the sensor active region to the readout member electrically. This may allow to properly spacing the Front End of the Line components, which may be degraded by a fluidic or liquid sample from the sensor active surface in the BEOL, which may be less prone to degradation by liquids.

The sensor chip may comprise an electrode for detection by capacitance at least partially formed in the Back End of the Line and arranged such that a capacity value of the electrode is influenceable by a detection event in the sensor active region. The capacitance of the electrode may be changed in the presence of a molecule close to the electrode or in contact with the electrode and therefore selectively in the presence of sensor events. However, it is possible to implement alternative detection schemes which do not include a capacitor, for instance a direct impact of a sensor event on the voltage acting on a gate region of a transistor, or the like.

When the sensor active region comprises a nanoelectrode, the dimensions of the electrode may be in the order of magnitude of nanometers, for instance may be less than 300 nm, for instance may be less or equal than 250 nm, or may be less or equal than 130 nm. The closer the size of the nanoelectrodes to the size of the molecule to detect, the more sensitive the resulting sensor will be.

The nanoelectrode may comprise copper material, particularly copper material being covered by the dielectric layer on which, in turn, a functionalization layer, like a self assembled monolayer (SAM) may be deposited. These materials may serve for enabling bonding of capture molecules.

The sensor chip may be manufactured in CMOS technology. CMOS technology, particularly the latest generations thereof, allow to manufacture structures with very small dimensions. A CMOS process may be a preferred choice. A BiCMOS process in fact is a CMOS process with some additional processing steps to add bipolar transistors. The same holds for CMOS processes with other embedded options like embedded flask, embedded DRAM, etc. In particular this may be relevant because the presence of an option often provides opportunities to use additional materials that come with the options "at zero cost". For instance, an appropriate high-k material (an insulating material with a high dielectric constant, for example aluminium oxide) that comes with an embedded DRAM process can be used "at zero cost" to cover the copper surface of the nanoelectrodes with a protective dielectric layer on which, subsequently, a functionalization layer or a SAM can be deposited (the function of the SAM would be to "functionalize" that sensor surface, for instance to be able to attach capture probe molecules).

The sensor device may be monolithically integrated on the basis of a semiconductor substrate, particularly comprising one of the group consisting of a group IV semiconductor (such as silicon or germanium), and a group III-group V semiconductor (such as gallium arsenide).

The biosensor chip or microfluidic device may be or may be part of a sensor device, a sensor readout device, a lab-on-chip, an electrophoresis device, a sample transport device, a sample mix device, a sample washing device, a sample purification device, a sample amplification device, a sample extraction device or a hybridization analysis device. Particularly, the biosensor or microfluidic device may be implemented in any kind of life science apparatus.

For any method step, any conventional procedure as known from semiconductor technology may be implemented. Forming layers or components may include deposition techniques like CVD (chemical vapour deposition), PECVD (plasma enhanced chemical vapour deposition), ALD (atomic layer deposition), or sputtering. Polishing may include CMP (chemical mechanical polishing). Removing layers or components may include etching techniques like wet etching, plasma etching, etc., as well as patterning techniques like optical lithography, UV lithography, electron beam lithography, etc.

Embodiments of the invention are not bound to specific materials, so that many different materials may be used. For conductive structures, it may be possible to use metallization structures, silicide structures or polysilicon structures. For semiconductor regions or components, crystalline silicon may be used. For insulating portions, silicon oxide or silicon nitride may be used.

The biosensor may be formed starting with a purely crystalline silicon wafer or an SOI wafer (Silicon On Insulator).

Any process technologies like CMOS, BIPOLAR, BICMOS may be implemented.

Next, further exemplary embodiments of the method will be explained. However, these embodiments also apply to the sensor chip.

Forming the continuous dielectric layer may be the very last step in chip processing and may be directly followed by the packaging procedure forming the electric connection element electrically connected to the electric connection structure through the continuous dielectric layer, by an ohmic and/or capacitive coupling. Thus, the generated sensor chip may be packaged directly after depositing the continuous dielectric layer. In other words, such a step may be the end step in the end of the line. The electric connection to periphery devices may then be performed via the electric connection structure directly attachable to the bond pads through the continuous dielectric layer.

The method may further comprise patterning the continuous dielectric layer. According to specific embodiments, such a patterning of specific portions may be performed, however maintaining the dielectric layer on the electric connection structure and on the sensor active region.

The method may further comprise forming the continuous dielectric layer by depositing an initial layer (for instance a tantalum layer) and by subsequently oxidizing the initial layer (thereby forming a tantalum oxide layer). Such a procedure can be performed once, or can be repeated twice, three times or more times, that is to say may be repeated. In such a scenario, tantalum deposition may be followed by oxidizing (oxidizing may be by oxidation techniques or by natural oxide growth in normal atmosphere and with ambient temperature), a further tantalum deposition may be followed by a further oxidizing procedure, and so on.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

FIG. 1 illustrates a cross-sectional view of a sensor device according to an exemplary embodiment of the invention.

FIG. 2 to FIG. 7 illustrate different layer sequences during a method of manufacturing a sensor chip according to an exemplary embodiment of the invention.

DESCRIPTION OF EMBODIMENTS

Figure 8:
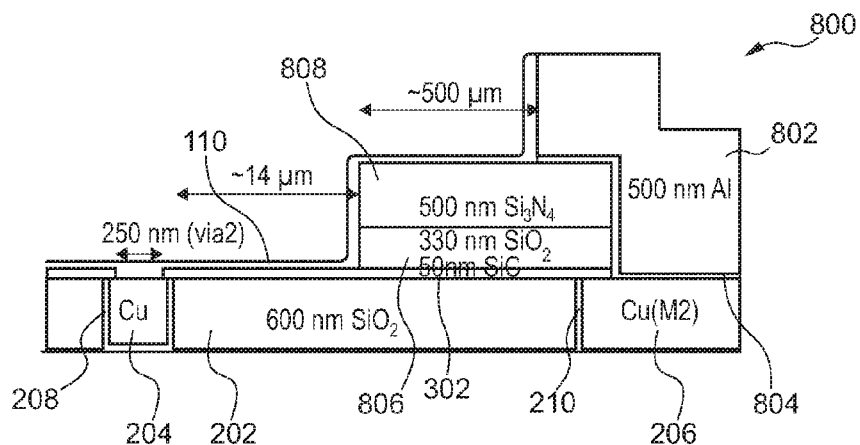
FIG. 8 illustrates a further cross-sectional view of a sensor chip according to another exemplary embodiment of the invention.

The illustration in the drawing is schematical. In different drawings, similar or identical elements are provided with the same reference signs.

The CMOS sensors top surface may be made of several materials:
  The bond pads may be made of aluminium or copper.
  The electrodes, that is to say the place where the detection occurs, may be made of a conductive material.
  The non-used surface between bond pads and electrodes may be made of a dielectric (for instance silicon oxide, silicon nitride or low-k dielectric).

Embodiments of the invention may cover the whole surface of the sensor with a continuous dielectric layer. This layer may be:
  Thin to reduce or minimize its influence on the detection at the electrodes.
  Thin to be able to do the bonding/bumping through it at the bond pads.
  Made of a high-k material, especially in case of a capacitive sensor to reduce or minimize its influence on the electrode capacitance.
  Made of the suitable material according to the sensing (for example pH sensitive material in case of a pH sensor). Thus, passivation and sensor functioning may be combined.
  Made of a stack of materials.

According to an exemplary embodiment of the invention, the same, continuous, dielectric layer may cover the bond pads and the electrodes.

FIG. 1 illustrates a sensor chip 100 for detecting particles according to an exemplary embodiment of the invention.

The sensor chip 100 comprises a substrate 102 having an upper main surface 120. A plurality of bonding pads 104 are arranged in a plurality of surface portions of the substrate 102 and are adapted for an electric connection to a respective bond wire 106.

Furthermore, the sensor chip 100 comprises a plurality of sensor electrodes 108 arranged in another surface portion of the silicon substrate 102. The sensor electrodes 108 are part of a capacitive sensor and are sensitive to the presence of the particles to be detected. Such particles may be included in a fluidic sample that may be provided in a sample accommodation space 124 above the sensor chip 100.

Moreover, a continuous high-k dielectric layer 110 made for example of tantalum oxide covers the entire upper surface 120 of the substrate 102 including covering the bonding pads 104 and the sensor electrodes 108.

The bond wires 106 are electrically connected to the bonding pads 104 through the continuous high-k dielectric layer 110. The thickness d of the continuous dielectric high-k layer 110 is 4 nm in the present embodiment. Components 104 and 108 are made from copper, which is prevented from corrosion by the continuous layer 110. The latter is made of a biocompatible impermeable material, namely tantalum oxide. Both, the sensor active region 108 as well as the dielectric layer 110 are formed in the Back End of the Line (BEOL). The entire sensor chip 100 is manufactured in CMOS technology.

The copper bond pads 104 and the copper electrodes 108 for biomolecule detection are provided on the surface of the substrate 102 and are covered by the continuous dielectric layer 110 on top of the sensor structure made of CMOS technology.

According to an exemplary embodiment of the invention, the whole surface 120 of the sensor 100 is covered with the continuous dielectric layer 110. This layer 110 is thin to minimize its influence on the detection at the electrodes 108. It is further thin to be able to do a bonding/bumping through it at the bond pads 104. The dielectric layer 110 is made of a high-k material in case of the capacitive sensor chip 100 to reduce or minimize its influence on the electrode capacitance. Exemplary embodiments of the invention may be implemented in any sensor, such as a biosensor, where the top surface 120 includes bond pads 104 and electrodes 108.

Embodiments of the invention may provide for a protection of the bond pads 104 and the electrodes 108. Metals tend to corrode and the layer 110 is a protective layer for the metallic electrodes 108 and the bond pads 104. In a biosensor 100 according to an exemplary embodiment, the electrodes 108 and the bond pads 104 may be made of copper, which may corrode in physiological liquids containing chlorine ions, and the dielectric layer 110 may prevent that corrosion.

The provision of the dielectric layer 110 has the further advantage that only one material is in contact with the external world. There is no need to test and to tune the biocompatibility of several materials (this can be crucial for implantable devices). No electrical reaction between several conducting materials exposed to a liquid has to be performed (if two metals are exposed to the same liquid, the same behaves like a battery).

Further, the layer prevents that any leakage of liquid into the chip occurs. In the state-of-the-art of CMOS technology, the dielectrics at the metal levels are porous low-k materials that do not seal the chip. Leakage along the seam between the electrodes and the dielectric around can also occur.

Furthermore, the dielectric layer may provide for a smooth and well-controlled electrode surface. The deposition of a thin layer may smoothen the defects and irregularities of the electrode surfaces 104, 108 and fill possible pinholes. Because this dielectric layer 110 is the very last step of the chip processing, it will not be damaged later. This is especially useful in some sensors where the detection electrodes 108 are first buried to build the bond pads 104 and then opened by an etching process, since in this case the etching process may make the electrode surface irregular.

Moreover, the dielectric layer 110 does not necessarily have to be fabcompatible. The contamination rules in CMOS fabs are very strict and some materials would not be allowed there even if they would be the best choice from the sensing point of view. Since in the present case, the dielectric layer 110 may be the very last step of the processing (without any etch later), its deposition can be done after the wafer has left the CMOS fab. The deposition is doable with low cost as the deposition tools of small factories, as with high cost deposition tools of CMOS standard factories.

As can be taken from FIG. 1, the bonding ball 106 goes through the dielectric layer 110 and touches the bond pads 104 on the chip 100. In other words, the bonding 106 may pierce through the layer 110.

In the following, referring to FIG. 2 to FIG. 7, layer sequences will be explained based on which a sensor chip according to an exemplary embodiment of the invention can be manufactured.

FIG. 2 illustrates a layer sequence 200 having a silicon oxide layer 202 in which a copper structure 204 and a further copper structure 206 are integrated, after formation of a respective lining 208, 210. A lateral diameter of the copper structure 204 is 250 nm, whereas a dimension of the copper structure 206 of a bond pad area 212 is 100 µm. Thus, FIG. 2 shows formation of a standard interconnect metal level.

To obtain a layer sequence 300 as shown in FIG. 3, starting from the layer sequence 200 shown in FIG. 2, a silicon carbide layer 302, a silicon oxide layer 304 and a silicon nitride layer 306 are deposited subsequently on the layer sequence 200. Moreover, a thin silicon oxide surface layer 308 is formed. FIG. 3 shows the deposition of a stack of the dielectric layers 302, 304, 306, 308. They can be low-k materials. Preferably, this stack 302, 304, 306, 308 contains silicon nitride material and is watertight.

In order to obtain a layer sequence 400 shown in FIG. 4, holes 402 having a diameter of 250 nm and holes 404 having a lateral dimension of 100 µm are etched as a basis for formation of the electrodes and the bond pads.

In order to obtain a layer sequence 500 shown in FIG. 5, an adhesion barrier 502 is deposited. Subsequently, copper material 504 is deposited, and electroplated.

To obtain a layer sequence 600 shown in FIG. 6, a CMP procedure ("Chemical Mechanical Polishing") is performed. Thus, a portion of the copper material 504 is removed, and a nanosensor electrode 602 as well as a bond pad structure 604 remain.

To obtain a layer sequence 700 shown in FIG. 7, a continuous dielectric layer 110 is deposited on the surface of the layer sequence 600.

Embodiments of the invention are particularly appropriate in cases like this when the sensing region 602 and the bonding region 604 are made of copper material, since copper is a reactive material and thus needs to be protected.

FIG. 8 illustrates a biosensor chip 800 according to another exemplary embodiment of the invention.

The metal 2 layer is similar as in FIG. 2. After metal 2, a passivation stack of silicon carbide 302, silicon oxide 806 and silicon nitride 808 is deposited. Then it is etched and aluminium is deposited to made aluminium bond pads 802. The, a large hole is opened in the silicon nitride 808 and silicon oxide 806 and small holes in the silicon carbide 302 are opened to get access to the electrodes. Finally, the continuous dielectric layer 110 is deposited.

In the following, further details regarding formation of the dielectric layer will be explained.

It is possible to perform an optional pre-reactive clean to remove contaminations and copper oxide. Furthermore, deposition of a tantalum layer, for instance with a thickness of 3 nm, is possible. Thereafter, the tantalum material may be oxidized into tantalum oxide. Subsequently, packaging with bonding through the tantalum oxide layer is possible.

However, a specifically advantageous way to form the tantalum oxide layer is the following:

Deposition of a layer of 1 nm of tantalum. This deposition may involve usually three steps in the same tool:

1. A pre-reactive clean can be used just before the deposition to remove any contamination and copper oxide.

2. A degas step which may be usually performed at that moment should be omitted because of its high temperature which might create height difference between the copper grains at their boundaries, what would weaken the thin dielectric layer.

3. The deposition of the tantalum itself.

A waiting time in a normal atmosphere is performed to let the native tantalum oxide grow for, for instance, 24 hours.

Then, a deposition of one (1) nm of tantalum may be performed. Without pre-reactive clean and without degas, a high performance may be achieved. This double deposition procedure may be such that if pinholes are present in the first tantalum layer, they will not be present at the same place in the second tantalum layer.

Then, an oxidation at a high temperature in an atmosphere containing oxygen may be performed. Here, it should be ensured that the full tantalum layer is oxidized but the copper below is ideally not oxidized. An example is a treatment for one (1) minute at 400° C. in an atmosphere with 5% oxygen.

Basically, a sequence for manufacturing a sensor according to an exemplary embodiment of the invention is cleaning, deposition of a layer, modification of the layer if necessary, and packaging with bonding through the dielectric layer.

Possible materials for the dielectric layer are high-k materials in the biosensor device using capacitive detection of biomolecules because the capacitance of the dielectric will be lower for a high-k material. The following materials may be used:

Tantalum oxide can be used. This is a high-k material, and the layer thickness can be between three (3) nm and ten (10) nm. The material has a high chemical stability, excellent passivation properties, and may be used in implantable devices. Such a material is available in fabs.

Alternatively, aluminium oxide can be used. This is also a high-k material, and a layer thickness can be around 3 to 10 nm. Such a material is available in fabs.

It is also possible to use silicon carbide. This has a somewhat smaller but also relative high k value, so the layer thickness should be lower than for high-k materials. Such a material is available in fabs as well.

Such a dielectric layer may be coated for example to improve it or to attach biomolecules to it. For example, a self-assembled monolayer may be deposited thereon.

One aspect of the invention is that the dielectric layer is kept on the bond pads, and therefore the dielectric layer deposition may be a very last step of the chip processing.

Referring to FIG. 9 to FIG. 12, it is also possible to pattern the dielectric layer 110 by etching.

Figure 9:
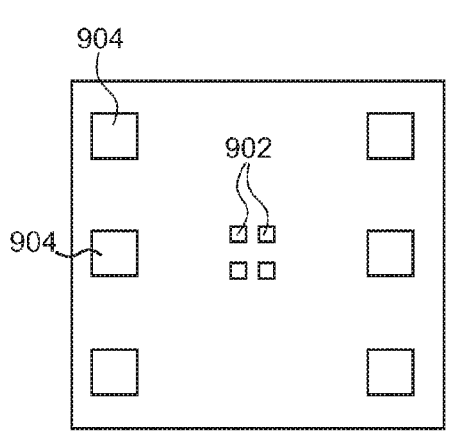
FIG. 9 to FIG. 12 show plan views of layer sequences of a sensor chip according to an exemplary embodiment of the invention.

FIG. 9 shows a plan view of a layer sequence 900. Sensing electrodes 902 are provided in a sensing area. Bond pads 904 are provided as well.

Figure 10:
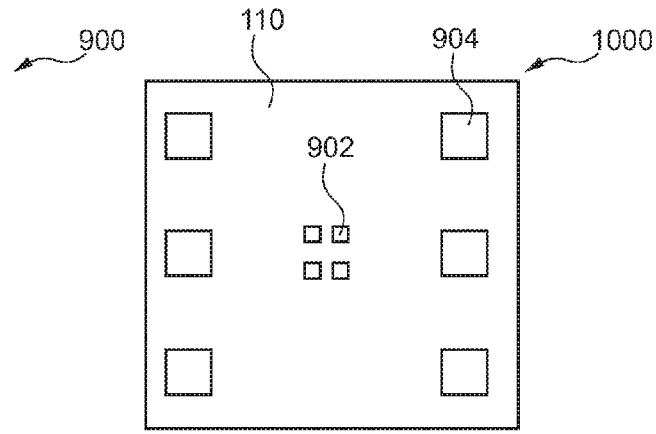

To obtain a layer sequence 1000 as shown in FIG. 10, a dielectric layer 110 is deposited thereon.

Figure 11:
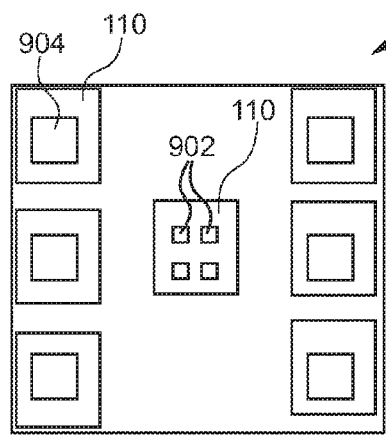

FIG. 11 shows a layer sequence 1100 in which the dielectric layer 110 is patterned to cover only the bond pads 904 and the sensor electrodes 902 with a common dielectric structure.

Figure 12:
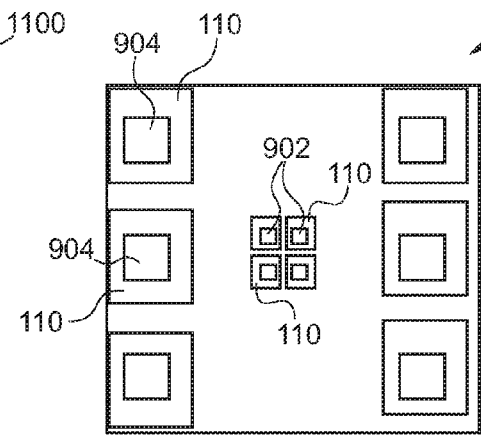

Alternatively, as shown in a layer sequence 1200 shown in FIG. 12, the dielectric layer 110 may be patterned to not cover all electrodes 902 with a continuous structure, but each of the sensor electrodes 902 is covered with a separate island of the dielectric layer 110.

Finally, it should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The words "comprising" and "comprises", and the like, do not exclude the presence of elements or steps other than those listed in any claim or the specification as a whole. The singular reference of an element does not exclude the plural reference of such elements and vice-versa. In a device claim enumerating several means, several of these means may be embodied by one and the same item of software or hardware. The mere fact that certain measures are recited in mutually different dependent claims does not indicate that a combination of these measures cannot be used to advantage.

The invention claimed is:

1. A sensor chip for detecting particles, the sensor chip comprising
   a substrate;
   an electric connection structure arranged in a surface portion of the substrate and adapted for an electric connection to an electric connection element;
   a sensor active region arranged in another surface portion of the substrate and being sensitive to the presence of the particles to be detected;
   a continuous dielectric layer covering the substrate including covering the electric connection structure and the sensor active region, the sensor active region being configured and arranged with the dielectric layer to detect, via the dielectric layer, a characteristic of biological particles in a solution exposed to the dielectric layer, wherein the electric connection structure and the sensor active region are arranged on the same side of the substrate;
   a silicon carbide layer in contact with the substrate;
   a first silicon oxide layer in contact with the silicon carbide layer;
   a silicon nitride layer in contact with the first silicon oxide layer; and
   a second silicon oxide layer in contact with the silicon nitride layer and with the continuous dielectric layer.

2. The sensor chip of claim 1, comprising the electric connection element, particularly a bumping structure or a bonding structure, electrically connected to the electric connection structure, particularly a bond pad, via capacitive coupling through the continuous dielectric layer.

3. The sensor chip of claim 1, wherein the continuous dielectric layer comprises a high-k material, particularly comprises at least one of the group consisting of tantalum oxide, aluminum oxide, and silicon carbide.

4. The sensor chip of claim 1, wherein the continuous dielectric layer has a thickness in a range between at least one of the following: about 1 nm and about 50 nm, about 2 nm and about 10 nm, less than about 5 nm.

5. The sensor chip of claim 1, wherein the sensor active region comprises at least one sensor electrode, and the sensor active region is further configured and arranged with the dielectric layer to detect the presence of a target particle.

6. The sensor chip of claim 1, wherein the sensor active region is a capacitive sensor region.

7. The sensor chip of claim 1, wherein at least one of the group consisting of the electric connection structure and the sensor active region comprises copper.

8. The sensor chip of claim 1, wherein the continuous dielectric layer comprises a biocompatible material.

9. The sensor chip of claim 1, wherein the continuous dielectric layer comprises an impermeable material.

10. The sensor chip of claim 1, wherein the sensor active region is arranged at an upper end of a Back End of the Line portion of the sensor chip.

11. The sensor chip of claim 1, comprising at least one of the group consisting of one or more capture molecules and a functionalization layer arranged on a portion of the dielectric layer above a surface of the sensor active region.

12. The sensor chip of claim 1, adapted as a biosensor chip.

13. The sensor chip according to claim 1, manufactured in CMOS technology.

14. The sensor chip of claim 1, wherein the continuous dielectric layer is made of a stack of several dielectric materials.

15. The sensor chip of claim 1, wherein the continuous dielectric layer comprises an impermeable material.

16. The sensor chip of claim 1, wherein the continuous dielectric layer is made of a single material.

17. An apparatus comprising:
   a substrate;
   dielectric material on the substrate;
   a sensor active region in a surface portion of the substrate and configured and arranged with the dielectric material to detect a type of particles in a solution exposed to the dielectric material, the dielectric material being configured and arranged to mitigate contact of the solution to the sensor active region; and
   an electric connector structure in a different surface portion of the substrate, adapted for an electric connection to an electric connection element, and configured and arranged with the dielectric material to couple a readout signal via the dielectric material, the readout signal being indicative of a type of particle detected via the sensor active region, the dielectric material being configured and arranged to mitigate contact of the solution to the electric connector structure, wherein the electric connector structure and the sensor active region are arranged on the same side of the substrate;
   a silicon carbide layer in contact with the substrate;
   a first silicon oxide layer in contact with the silicon carbide layer;
   a silicon nitride layer in contact with the first silicon oxide layer; and
   a second silicon oxide layer in contact with the silicon nitride layer and with the dielectric material.

18. The apparatus of claim 17, further including a functionalization material on a portion of the dielectric material that is on the sensor active region, the functionalization material being configured and arranged to couple to biological particles in the solution and therein facilitate detection of the presence of the particles via the dielectric material.

19. The apparatus of claim 17, wherein the dielectric material is a continuous layer covering the sensor active region and the electric connector structure and includes an impermeable material configured and arranged to prevent contact between the solution and the substrate.

20. The apparatus of claim 17, wherein the dielectric material has a thickness of at least 1 nm and less than 5 nm, and the sensor active region is further configured and arranged with the dielectric layer to detect the presence of a target particle.

21. The apparatus of claim 20, wherein the target particle is one of: genes, DNA, RNA, proteins, enzymes, cells, bacteria, and a virus.

* * * * *